US012766699B2

(12) United States Patent
Welchman et al.

(10) Patent No.: US 12,766,699 B2
(45) Date of Patent: Oct. 20, 2026

(54) ARRANGEMENT FOR SUPPORTING A SURGICAL ROBOT

(71) Applicant: CMR Surgical Limited, Cambridge (GB)

(72) Inventors: Daniel Christopher Welchman, Cambridge (GB); Roger James Springett, North Northamptonshire (GB); Andrew Robert Mawby, London (GB); Silvia Perez, Cambridge (GB); Pedro Angel Riera Martinez, London (GB); Júlia Masvidal I Andreu, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 223 days.

(21) Appl. No.: 18/714,858

(22) PCT Filed: Dec. 2, 2022

(86) PCT No.: PCT/GB2022/053072

§ 371 (c)(1),
(2) Date: May 30, 2024

(87) PCT Pub. No.: WO2023/099914

PCT Pub. Date: Jun. 8, 2023

(65) Prior Publication Data

US 2025/0026003 A1 Jan. 23, 2025

(30) Foreign Application Priority Data

Dec. 2, 2021 (GB) ..................................... 2117436

(51) Int. Cl.
*B25J 9/00* (2006.01)
*A61B 34/30* (2016.01)
*A61B 50/13* (2016.01)
*B25J 5/00* (2006.01)
(Continued)

(52) U.S. Cl.
CPC ............. *B25J 9/0009* (2013.01); *A61B 34/30* (2016.02); *A61B 50/13* (2016.02); *B25J 5/007* (2013.01); *F16M 3/00* (2013.01); *F16M 11/42* (2013.01)

(58) Field of Classification Search
CPC ......... B25J 9/0009; B25J 5/007; A61B 34/30; A61B 50/13; F16M 3/00; F16M 11/42
(Continued)

(56) References Cited

U.S. PATENT DOCUMENTS

| | | | | |
|---|---|---|---|---|
| 6,581,888 B1 * | 6/2003 | Castillo | A47G 23/0225 | 248/910 |
| 6,840,487 B2 * | 1/2005 | Carnevali | B60R 11/0241 | 248/346.06 |

(Continued)

FOREIGN PATENT DOCUMENTS

| | | | |
|---|---|---|---|
| GB | 1489950 | A | 10/1977 |
| KR | 20210096240 | A | 8/2021 |
| WO | 2004030872 | A1 | 4/2004 |

OTHER PUBLICATIONS

Search Report dated Apr. 26, 2022, for GB Patent Application No. 2117436.2.

(Continued)

*Primary Examiner* — Anita M King
(74) *Attorney, Agent, or Firm* — Renner, Otto, Boisselle & Sklar, LLP

(57) ABSTRACT

An arrangement for supporting a surgical robot, the arrangement comprising: a planar member on which the surgical robot is supported; a bladder coupled to a bottom surface of the planar member, the bladder comprising: an external membrane having a surface which opposes the bottom surface of the planar member and which is configured to comply with an uneven surface that it is in contact with; an internal cavity defined by the external membrane, the inter-
(Continued)

nal cavity holding a plurality of solid particles and being configured to hold a plurality of fluid particles; and an opening in the external membrane, the opening being configured to enable the extraction of one or more of the fluid particles so as to cause an increased frictional engagement between the plurality of solid particles, thereby stabilising the surgical robot on the uneven surface.

18 Claims, 7 Drawing Sheets

(51) Int. Cl.
*F16M 3/00* (2006.01)
*F16M 11/42* (2006.01)
(58) Field of Classification Search
USPC .......................................................... 248/396
See application file for complete search history.

(56) References Cited

U.S. PATENT DOCUMENTS

| | | | | |
|---|---|---|---|---|
| 6,986,308 | B1 * | 1/2006 | King | A47G 23/0608 108/43 |
| 7,988,106 | B2 * | 8/2011 | Carnevali | F16M 11/041 248/910 |
| 9,452,797 | B2 * | 9/2016 | Kim | B62D 57/02 |
| 10,067,409 | B2 * | 9/2018 | Elias | F16M 11/242 |
| 10,716,635 | B2 | 7/2020 | Rosenberg | |
| 2013/0162015 | A1 | 6/2013 | Kim et al. | |
| 2019/0274866 | A1 | 9/2019 | Chang et al. | |
| 2019/0314112 | A1 | 10/2019 | Wellborn et al. | |
| 2022/0194665 | A1 * | 6/2022 | Gull | B65D 33/02 |
| 2023/0415330 | A1 * | 12/2023 | Grant | A61B 34/30 |

OTHER PUBLICATIONS

International Search Report and Written Opinion mailed Mar. 13, 2023, for International Application No. PCT/GB2022/053072.
Ahmad Najmuddin et al.; Experimental Development of Stiffness Adjustable Foot Sole for Use by Bipedal Robots Walking on Uneven Terrain; IEEE; Dec. 16-18, 2012; pp. 248-253.
Fabrizio Putzu et al.; Soft Particles for Granular Jamming; Centre for Advanced Robotics; 2019; pp. 65-74.
Raghav Mishra et al.; Vibration Improves Performance in Granular Jamming Grippers; Arvix. org; Sep. 22, 2021.

* cited by examiner

ARRANGEMENT FOR SUPPORTING A SURGICAL ROBOT

This application is a national phase of International Application No. PCT/GB2022/053072 filed Dec. 2, 2022, which claims priority to United Kingdom Application No. 2117436.2 filed Dec. 2, 2021, each of which is hereby incorporated herein by reference in its entirety.

FIELD OF THE INVENTION

This invention relates to an arrangement for supporting a surgical robot on an uneven surface, and in particular to an arrangement comprising a bladder that can be compacted in order to stabilise the robot on the uneven surface.

BACKGROUND OF THE INVENTION

The field of surgical robotics is rapidly expanding, with robotic systems offering many advantages over traditional surgical means including shorter hospitalisation times, faster recovery, and reduced scarring after surgery. Known surgical robotic systems comprise a surgeon's console, one or more robot arms, and one or more surgical instruments comprising an end effector for attachment to the robot arms. The one or more robot arms are operated using controllers located on the surgeon's console and are used to manipulate the position and orientation of their respective end effectors. Thus, there is a master-slave control relationship between the surgeon's console and the end effectors.

In a known surgical robotic system, each robot arm within the system is mounted to a respective surgical cart. The robot arm and the cart to which it is mounted can jointly be referred to as a surgical robot. The surgeon's console is typically a stationary member of the robotic system, but by contrast each surgical robot is moveable by virtue of its respective surgical cart. That is, the surgical carts allow for each surgical robot to be moved around an operating theatre so that it can be stationed in a desired position, next to the operating table on which a patient is located, in advance of a surgical procedure. In addition to this, the surgical carts allow for movement of the surgical robots between operating theatres and hospital buildings. Once it has been moved to a desired position for a surgical procedure, a surgical robot must be secured in position for the duration of that procedure.

When the surgical robot has been secured in a desired position, it is important to ensure its stability. A stable robot is one that does not tilt, turn, or perform accidental movements during a surgical procedure. The stability of the surgical cart in particular is of utmost importance to the performance of the surgical robotic system because, when an end effector is in direct contact with the patient during a surgical procedure, any inadvertent movement of its respective surgical cart will be transmitted to the end effector via the robot arm. The likelihood of an inadvertent movement of the cart is increased when the surgical robot is positioned on an irregular or uneven surface. Thus, if the cart is unable to maintain stability on an uneven surface, then this could result in undesired movements of the end effector, which in turn could have catastrophic implications for the patient.

There is a need to provide an arrangement that can improve the stability of a surgical robot on an irregular or uneven surface.

SUMMARY OF THE INVENTION

According to a first aspect, there is provided an arrangement for supporting a surgical robot, the arrangement comprising: a planar member on which the surgical robot is supported; a bladder coupled to a bottom surface of the planar member, the bladder comprising: an external membrane having a surface which opposes the bottom surface of the planar member and which is configured to comply with an uneven surface that it is in contact with; an internal cavity defined by the external membrane, the internal cavity holding a plurality of solid particles and being configured to hold a plurality of fluid particles; and an opening in the external membrane, the opening being configured to enable the extraction of one or more of the fluid particles so as to cause an increased frictional engagement between the plurality of solid particles, thereby stabilising the surgical robot on the uneven surface.

The bladder may be coupled to the bottom surface of the planar member by an upper surface of the external membrane, and the shape of the upper surface of the external membrane may match the shape of the bottom surface of the planar member.

The bladder may be coupled to the bottom surface of the planar member by an upper surface of the external membrane such that a portion in the middle of the bottom surface of the planar member is exposed.

The planar member may comprise one or more apertures such that a moveable element is able to extend through each aperture, and the external membrane may be shaped so that the bladder does not interfere with the moveable elements as its level of pressurisation is varied.

The one or more apertures may comprise four apertures.

The internal cavity may further comprise a plurality of compartments and one or more internal membranes separating each compartment from its adjoining compartments, the one or more internal membranes being permeable to the fluid particles but impermeable to the solid particles.

The arrangement may be further configured to apply a first pressure to a first end of the bladder that is different to a second pressure that is applied to a second end of the bladder.

The arrangement may comprise a plurality of bladders, and the level of pressurisation of each bladder may be independent of the level of pressurisation of the remaining bladders.

The bottom surface of the planar member may comprise a plurality of vertices and each bladder of the plurality of bladders may be coupled to a respective vertex.

The arrangement may further comprise a mechanism for applying a mechanical vibration to the solid particles.

The one or more bladders may be removably coupled to the bottom surface of the planar member.

The fluid particles may be gas particles.

The one or more bladders may further comprise a reinforcement material attached to the external membrane, the reinforcement material being configured to maintain the shape of the bladder as its level of pressurisation is varied.

The bottom surface of the planar member may be in the shape of a quadrilateral.

The plurality of solid particles may be independent granular particles.

The plurality of solid particles may form a plurality of layers of particles.

The arrangement may further comprise one or more sensors configured to detect when the one or more bladders are in contact with the surface.

The planar member may be coupled to a mechanical brake system that comprises a linear lifting column that is coupled to an upper surface of the planar member.

The dimensions of the external membrane may be such that, when the linear lifting column is in a retracted configuration, the one or more bladders are not in contact with the surface.

The arrangement may further comprise a control unit configured to control the extraction of one or more of the fluid particles from the bladder.

The arrangement may further comprise a vacuum source coupled to the opening and configured to extract one or more of the fluid particles from the bladder.

According to a second aspect, there is provided a method for stabilising a surgical robot on an uneven surface, the method comprising: stopping the motion of the surgical robot relative to the surface; and lowering a linear lifting column towards the surface, the linear lifting column being coupled to an arrangement comprising a planar member on which the surgical robot is supported and a bladder coupled to a bottom surface of the planar member, the bladder comprising: an external membrane having a surface which opposes the bottom surface of the planar member and which is configured to comply with an uneven surface that it is in contact with, an internal cavity defined by the external membrane and holding a plurality of solid particles and being configured to hold a plurality of fluid particles and an opening in the external membrane that is configured to enable the extraction of one or more of the fluid particles such that the bladder contacts and conforms to the surface, thereby stabilising the surgical robot on the surface.

The method may further comprise, when the bladder contacts and conforms to the surface, extracting one or more fluid particles from the bladder so as to cause an increased frictional engagement between the plurality of solid particles.

BRIEF DESCRIPTION ON THE FIGURES

The present invention will now be described by way of example with reference to the accompanying drawings. In the drawings.

DETAILED DESCRIPTION

Figure 1:
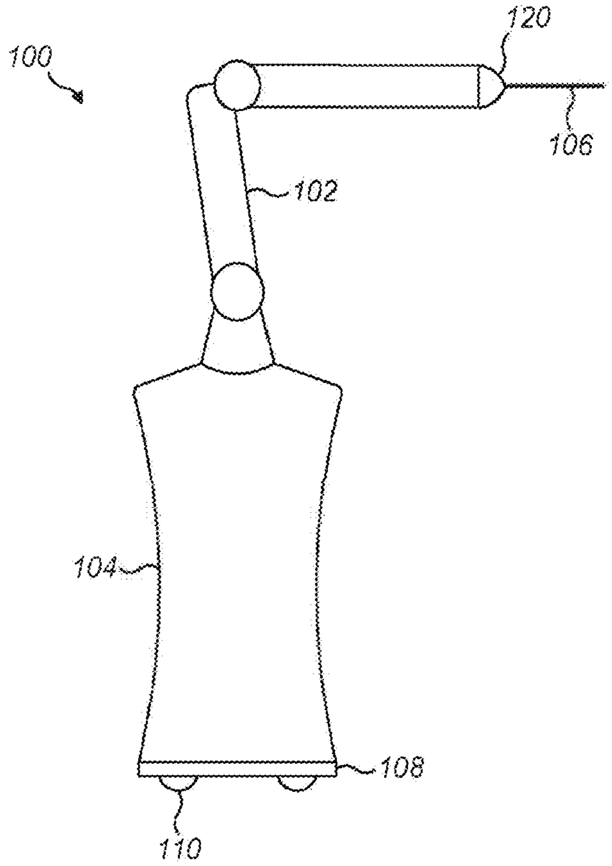
FIG. 1 illustrates the arrangement of a surgical robot.

The arrangement of a surgical robot to be implemented within a surgical robotic system is illustrated in FIG. 1. The surgical robot 100 comprises a robot arm 102 with a plurality of rigid limbs which are coupled together by a plurality of joints. In FIG. 1, the surgical robot comprises three limbs that are coupled together by two joints. However, alternative examples of surgical robots may comprise any number of limbs and corresponding joints. The joints are configured to apply motion to the limbs. The robot arm 102 is coupled at its proximal end to a surgical cart 104 and at its distal end to a surgical instrument 106. The surgical instrument 106 is attached to the robot arm 102 by an attachment 120 located at the distal end of the robot arm. The attachment 120 comprises a drive assembly for driving the articulation of the surgical instrument 106.

The surgical instrument 106 comprises an end effector that is suitable for performing a surgical procedure. The end effector may take any suitable form. For example, the end effector may be smooth jaws, serrated jaws, a gripper, a pair of shears, a pair of scissors, a needle for suturing, a laser, a knife, a stapler, a cauteriser or a suctioner. The end effector may alternatively be an electrosurgical instrument such as a pair of monopolar scissors. The robot arm 102 transfers drive to the end effector via the drive assembly interface located within the attachment 120 at the distal end of the arm. The robot arm 102 is actuated by a number of drive sources and sensors that are distributed within the arm. The drive sources can be controlled by software that is implemented in dependence on inputs from the sensors located within the arm, and from an operator that issues commands at a surgeon command interface. The surgeon command interface may form part of a surgeon's console.

The robot arm 102 is mounted on a surgical cart 104. In FIG. 1 the surgical cart 104 has one robot arm 102 mounted to it. In other examples, there may be more than one robot arm mounted to the surgical cart 104. The surgical cart 104 allows the surgical robot 100 to be moved with respect to the surface on which it is in contact. For example, the surgical cart 104 allows the surgical robot 100 to be moved along the floor of an operating theatre, and between operating theatres. The surgical cart 104 may also house electronic components that form the drive system of the robot arm 102 and its associated surgical instrument. As well as enabling movement of the surgical robot 100, the surgical cart 104 is also configured to secure the robot in a position that is desirable for a surgical procedure.

In addition to the robot arm 102, the surgical cart 104 is further coupled to a planar member 108 and one or more moveable elements 110. The moveable elements 110 are mechanical components that enable the movement of the surgical cart 104 relative to a floor surface. In one example, the moveable elements 110 are wheels. However, it will be appreciated that the moveable elements 110 may alternatively be any component that is capable of moving the surgical cart 104. The planar member 108 is connected to the lowermost surface of the surgical cart 104. The planar member 108 is configured as a flat plate and is therefore commonly referred to as a base plate. The planar member 108 may further comprise one or more apertures through which the moveable elements 110 can extend. Thus, the moveable elements 110 are not directly connected to the planar member 108 and can be moved independently of the planar member. Correspondingly, the planar member 108 can be moved independently of the moveable elements 110.

Figure 2A:
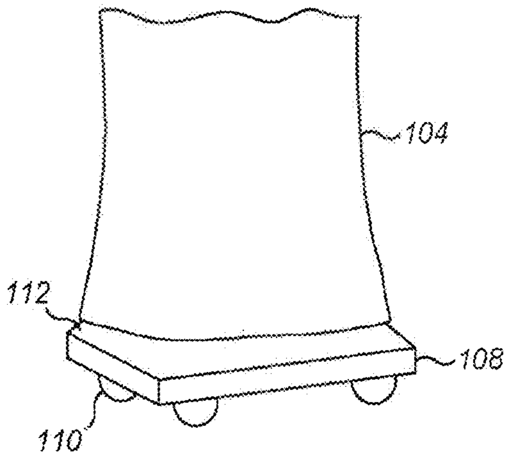
FIGS. 2A and 2B illustrate a first arrangement for supporting the surgical robot of FIG. 1 on a surface.
Figure 2B:
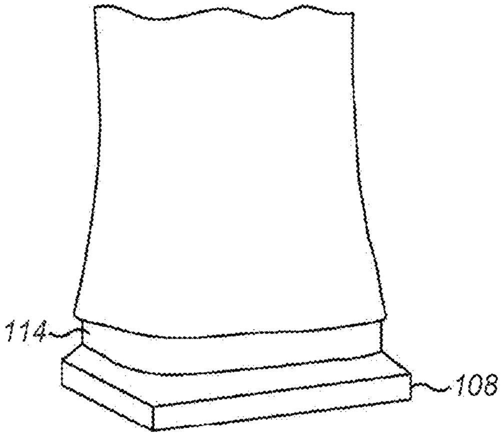

FIGS. 2A and 2B illustrate a first arrangement for supporting the surgical robot of FIG. 1 on a surface. The surgical cart 104 of the surgical robot is secured in a desired position by a mechanical brake system which is coupled to the planar member 108. The arrangement and execution of the mechanical brake system is demonstrated in FIGS. 2A and 2B, which illustrate a lower portion of the surgical cart 104 attached to its corresponding planar member 108 and moveable elements 110. FIG. 2A illustrates the configuration of the lower portion of the surgical cart 104 before the mechanical brake system has been actuated. That is, in FIG. 2A the surgical cart is free to move relative to the floor surface on which it is in contact. FIG. 2B illustrates the configuration of the lower portion of the surgical cart 104 after the mechanical brake system has been actuated. In this second configuration, the cart 104 and the surgical robot 100 as a whole are secured in a desired position.

The mechanical brake system forms part of the surgical robot 100 and comprises a skirt 112. The skirt 112 is located between the main body of the surgical cart 104 and the planar member 108, such that the main body of the cart is coupled to the planar member by the skirt. The skirt 112 comprises an outer surface which extends around and downwardly of the main body of the cart. The outer surface of the skirt 112 also extends outwardly from the main body of the cart as its distance from the main body of the cart 104 increases, such that the area encompassed by the lower surface of the skirt 112 is greater than the area encompassed by the bottom surface of the cart 104 from which the skirt extends. In FIG. 2A the bottom surface of the planar member 108 therefore also has a greater surface area than the area of the bottom surface of the main body of the cart 104. This increased surface area acts to improve the stability of the surgical robot 100 when the planar member 108 is in contact with the floor surface.

The mechanical brake system further comprises a linear lifting column 114. The linear lifting column 114 is rigidly connected to the skirt 112 of the surgical cart 104 and is slidably connected to the main body of the surgical cart 104. The linear lifting column 114 is therefore also connected to the planar member 108 via the skirt 112. The linear lifting column 114 has a smaller cross-sectional area than the main body of the cart 104. That is, the area of the lifting column 114 in a plane that is parallel to the lower surface of the skirt 112 is smaller than the corresponding area of the main body of the surgical cart 104. This smaller surface area means that, in the configuration illustrated in FIG. 2A, the linear lifting column 114 can be retracted within the main body of the surgical cart 104. In one example, the linear lifting column 114 is hollow, such that the internal area of the surgical cart 104 is minimally reduced by the presence of the column. In an alternative example, the linear lifting column 114 is solid.

In FIG. 2A, movement of the surgical robot 100 relative to the floor surface on which it is in contact is enabled because the moveable elements 110 that are coupled to the surgical cart 104 are exposed. The moveable elements 110 can therefore be used to move the robot.

FIG. 2B illustrates the configuration of the lower portion of the surgical cart 104 when the mechanical brake system is activated. The activation of this system involves lowering the linear lifting column 114 so that it protrudes past the main body of the cart 104. The lowering of the lifting column results in a lowering of the skirt 112 and the planar member 108 which is coupled to the skirt. The lifting column 114, the skirt 112 and the planar member 108 are not directly connected to the moveable elements 110. Thus, the arrangement of the lifting column 114, the skirt 112 or the planar member 108 can be moved independently of the moveable elements 110. That is, the moveable elements 110 can be held stationary and the lifting column 114 can be lowered until the lowermost surface of the planar member 108 extends past than the bottom of the moveable elements. The lowering of the lifting column 114 therefore results in the moveable elements 110 being lifted off the floor surface, such that the planar member 108 is instead used to support the load of the surgical robot. In addition to the lowering of the lifting column 114, the mechanical brake system may be configured to actively retract the moveable elements 110 to assist in their separation from the floor surface. This retraction may be performed simultaneously with the lowering of the lifting column 114. The retraction may alternatively be performed in advance or after the lowering of the lifting column 114.

In one example, the mechanical brake system is activated by an operator. In this example the mechanical brake system may be connected to an interface such as a button or a lever that enables the system to be actuated by the operator. In an alternative example, the mechanical brake system may be automatically activated. The interface may be located at the surgeon's console, or alternatively on the surgical cart 104. In one example, the mechanical brake system comprises integrated sensors that are configured to detect when the planar member 108 has contacted a floor surface. In one example, one or more force sensors are located on the lowermost surface of the planar member 108 such that they can detect when the planar member comes into contact with a floor surface by measuring a force value that exceeds a predetermined threshold. In other examples, alternative types of sensors may be used to detect when the planar member has contacted a floor surface, such as one or more light detectors, ultrasound sensors or UWB signal sensors. Once the planar member 108 has contacted the surface, the integrated sensors can provide feedback to the controllers of the mechanical brake system to indicate that the act of lowering of the linear lifting column 114 can be terminated. In another example, the mechanical brake system is configured so that the lifting column 114 can only be lowered to a predetermined maximum distance from the body of the surgical cart 104. In a further example, the lowering of the lifting column 114 may be both activated and terminated by an operator. That is, activation and termination of the brake mechanism may be actuated at a surgeon's console, or alternatively via an interface on the surgical cart 104.

During deactivation of the mechanical brake system, the lifting column 114 is raised which results in a raising of the skirt 112 and the planar member 108 until the moveable elements 110 are exposed. This action may optionally be synchronised with or supplemented by the active deployment of the moveable elements 110.

Figure 3A:
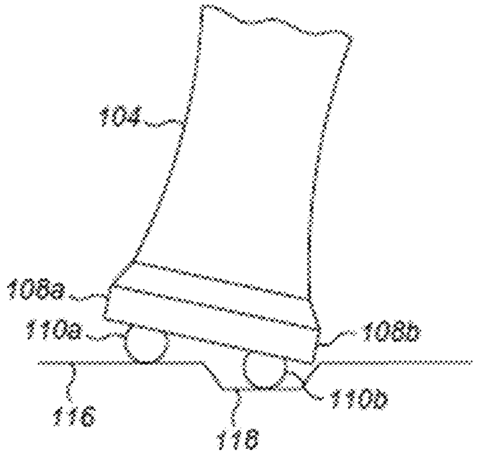
FIGS. 3A and 3B illustrate a disadvantage associated with the first arrangement illustrated in FIGS. 2A and 2B.
Figure 3B:
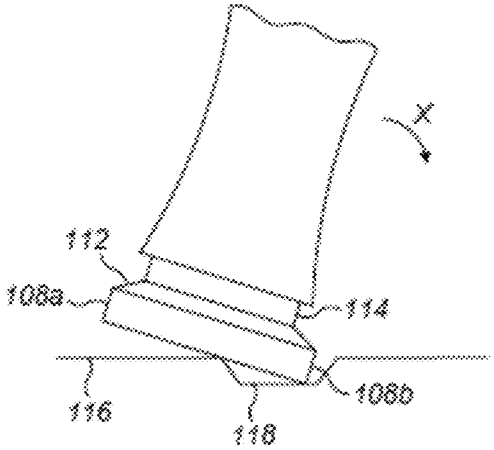

A disadvantage associated with the arrangement of the surgical cart illustrated in FIGS. 2A and 2B is illustrated in FIGS. 3A and 3B. The flexibility of the surgical cart that is provided by the planar member 108 in isolation, when it is in contact with an uneven floor surface, is very low. In other words, when the planar member is in contact with an uneven floor surface it is not able to adapt to the surface shape of relief in order to maintain the stability of the surgical robot.

In FIG. 3A movement of the surgical robot relative to the floor surface with which it is in contact is enabled because the one or more moveable elements 110 are exposed. The surgical cart 104 is positioned over a floor surface that comprises a first portion 116 of higher relative elevation and a second portion 118 of lower relative elevation. That is, the first portion 116 of the floor surface has a higher elevation than the second portion 118. A first part 108*a* of the planar member which is coupled to a first moveable element 110*a* is positioned over the first portion 116 of the floor surface. Correspondingly, a second part 108*b* of the planar member which is coupled to a second moveable element 110*b* is positioned over the second portion 118 of the floor surface. It can be seen that the surgical robot is orientated at a non-zero angle to the vertical by virtue of the difference in elevation between the first and second parts 108*a*, 108*b* of the planar member.

In FIG. 3B, the mechanical brake system has been activated and the planar member 108 has been lowered so that it is in contact with the floor surface. However, the planar member 108 is unable to adapt to the uneven nature of the surface. That is, the second part 108*b* of the planar member is in contact with the second portion 118 of the floor surface, but the first part 108*a* is not in contact with the corresponding first portion 116. Thus, the centre of gravity of the surgical robot is located over the second part 108*b* of the planar member, which results in the tilting of the surgical cart, and subsequently the robot arm, in a direction X. The lack of flexibility of the planar element 108 therefore reduces the overall stability of the surgical robot on the surface.

To overcome the above problem, an arrangement has been devised for stabilising a surgical robot on an uneven surface. Various examples of the devised arrangement are illustrated in FIGS. 4A to 12.

Figure 4A:
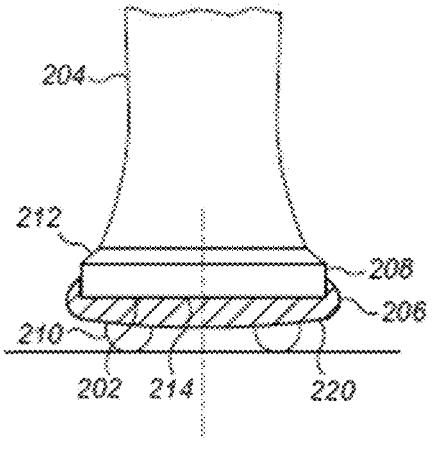
FIGS. 4A and 4B illustrate a second arrangement for supporting a surgical robot on a flat and an uneven surface, respectively.
Figure 4B:
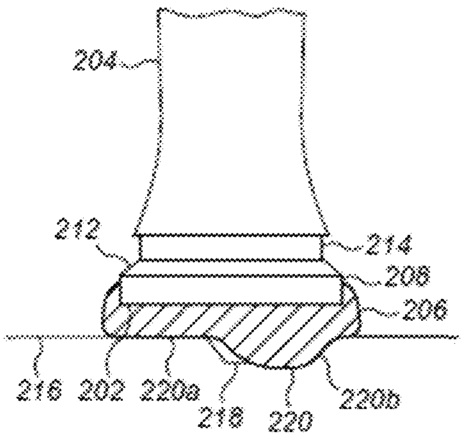

A second arrangement for supporting the surgical robot of FIG. 1 on a surface is illustrated in FIGS. 4A and 4B. As with FIGS. 2A-3B, FIGS. 4A and 4B illustrate the configuration of the lower portion of the surgical cart 204. FIG. 4A illustrates the configuration of the lower portion of the surgical cart 204 before the mechanical brake system has been actuated. With the exception of its lower portion, the surgical cart 204 corresponds to the surgical cart 104 illustrated in FIGS. 1 to 2B. The surgical cart 204 forms part of a surgical robot as illustrated in FIG. 1. The surgical cart 204 comprises a mechanical brake system as described above with respect to FIGS. 2A and 2B. The surgical cart 204 is further coupled to one or more moveable elements 210. The moveable elements 210 are mechanical components that enable the movement of the surgical cart 204 relative to a floor surface. In one example, the one or more moveable elements 210 are wheels.

The arrangement in FIGS. 4A and 4B comprises a planar member 208 at the bottom of the surgical cart 204 on which the surgical robot is mounted. The planar member 208 has a bottom surface 202 which is the surface of the planar member that is furthest from the skirt 212. The skirt 212 corresponds to skirt 112 illustrated in FIG. 2A. The arrangement further comprises a bladder 206 coupled to the bottom surface 202 of the planar member. The bladder 206 may be coupled to the bottom surface 202 of the planar member by any suitable means. In one example, the bladder 206 is glued to the bottom surface 202 of the planar member. In another example, the bladder 206 is attached to the bottom surface of the planar member by one or more fasteners, such as screws or Velcro-type attachments which enable the easy detachment and reattachment of the bladder to the planar member for cleaning purposes. The bladder 206 extends below the bottom surface of the planar member, away from the skirt 212 and towards the floor surface.

The bladder 206 comprises an external membrane, an internal cavity that is defined by the external membrane and an opening in the external membrane. The external membrane is formed of one or more layers of material and defines a housing within which the remaining features of the internal bladder are located. The external membrane comprises at least two opposing surfaces. Each surface comprises an outer side and an inner side. The inner side of each surface faces the internal cavity. The outer side of each surface faces away from the internal cavity and towards the environment in which the surgical robot is located. As illustrated in FIG. 4A, the dimensions of the external membrane are such that, when the linear lifting column 214 (FIG. 4B) is in a retracted configuration as illustrated in FIG. 4A, the bladder is not in contact with the floor.

A first surface of the external membrane is coupled to the bottom surface 202 of the planar member. More specifically, the outer side of the first surface of the external membrane is coupled to the bottom surface 202. The first surface of the external membrane therefore ensures that the bladder 206 is coupled to the surgical robot. The external membrane further comprises a second surface 220 which opposes the first surface. The second surface 220 therefore opposes the bottom surface 202 of the second planar member.

FIG. 4B illustrates the configuration of the lower portion of the surgical cart 204 when the mechanical brake system is activated, and the cart is placed on an uneven floor surface. The floor surface comprises a first portion 216 of higher relative elevation and a second portion 218 of lower relative elevation. The planar member 208 and the bladder 206 are lowered and the moveable elements 210 are retracted, so that the bladder 206 is placed in contact with the floor surface. More specifically, the second surface 220 of the bladder 206 is in contact with the floor surface. The second surface 220 is configured to comply with an uneven surface that it is placed in contact with. That is, a first part of the second surface 220*a* that is positioned over the first portion 216 has adapted to the shape of the first portion. A second part of the second surface 220*b* that is positioned over the second portion 218 has adapted to the shape of the second portion. The mechanism of the bladder that enables this compliance is described in further detail below. The centre of gravity is located over a central portion of the planar member, and so no tilting of the surgical cart is experienced. Thus, the stability of the cart is ensured.

The internal cavity of the bladder is defined by the external membrane. The internal cavity holds a plurality of solid particles. The solid particles are confined within the internal cavity. That is, the solid particles are permanently restrained within the internal cavity. The internal cavity is further configured to hold a plurality of fluid particles. The number of fluid particles located within the internal cavity may be varied to vary the pressurisation of the bladder. In a first state, the bladder may not comprise any fluid particles. The absence of fluid particles causes the external membrane to contract and the internal volume of the bladder to decrease. In this state the bladder can be described as being deflated. In a second state, the bladder may comprise a plurality of fluid particles in addition to its solid particles. The increase in fluid particles causes the external membrane to expand and the internal volume of the bladder to increase. In this state the bladder can be described as being inflated. The bladder further comprises an opening in the external membrane. The opening is configured to enable the extraction of one or more of the fluid particles so as to cause compaction of the bladder.

The bladder 206 utilises the concept of vacuum jamming. Vacuum jamming is a term used to describe the physical process by which the density or packing fraction of solid particles within a sealed vessel is increased. The density of solid particles within the vessel can be increased by decreasing the corresponding number of fluid particles. This decreases the volume of the vessel, and therefore the mass of solid particles per unit volume. The increase in density of solid particles results in compaction of those particles, which prevents their flow under an applied stress. That is, the compaction of solid particles results in an increased frictional engagement between the particles. The compaction therefore causes the internal cavity of the sealed vessel to behave as a solid. There are many mechanisms that can be used to increase the density of solid particles within the bladder. An example of a mechanism that may be used is a negative pressure machine, such as a vacuum source. The removal of fluid particles by the vacuum source results in a reduction in space between adjacent particles within the bladder, leaving them tightly packed together within the external membrane. The volume of the vessel is therefore reduced. If the sealed vessel is in contact with a floor surface when the vacuum source is applied, then the extraction of fluid particles from the vessel will cause the solid particles within the internal cavity to compact against that surface. This causes the surface of the vessel that is in contact with the surface to assume the shape of the floor surface.

The implementation of a bladder utilising the vacuum jamming concept described above is advantageous because such an apparatus is highly compliant in a non-vacuum state whilst also providing stability in the vacuum state. That is, the shape and configuration of the bladder is highly variable when it is inflated but is set in a compacted shape when it is deflated in order to provide a firm structure on which a surgical robot can be mounted. The state of the bladder can be varied in dependence on whether or not the mechanical brake system of the surgical cart has been activated. When the mechanical brake is not activated, as illustrated in FIG. 4A, the bladder may be in an inflated state. When the mechanical brake is activated, as illustrated in FIG. 4B, the bladder may be in a deflated state. The bladder is especially suited for stabilisation of a surgical cart because it can remain compliant whilst the cart is being moved and whilst it is being adapted to the profile of a floor surface but can be compacted once it has been suitably adapted to provide strength and stability to the base of the cart once it has been located in a desired position. Thus, the bladder can be used to stabilise the cart even if the surface that it is in contact with is irregular.

A number of different exemplary arrangements of bladders using the vacuum jamming concept described above can be applied to the base of a surgical cart. Such examples are described in more detail below.

Figure 5:
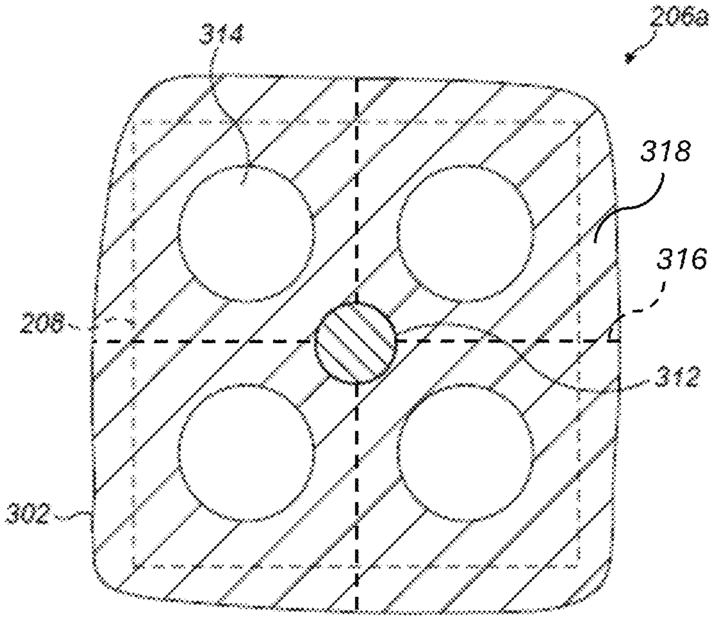
FIG. 5 illustrates a first example of a bladder suitable for the arrangement illustrated in FIGS. 4A and 4B.
Figure 6:
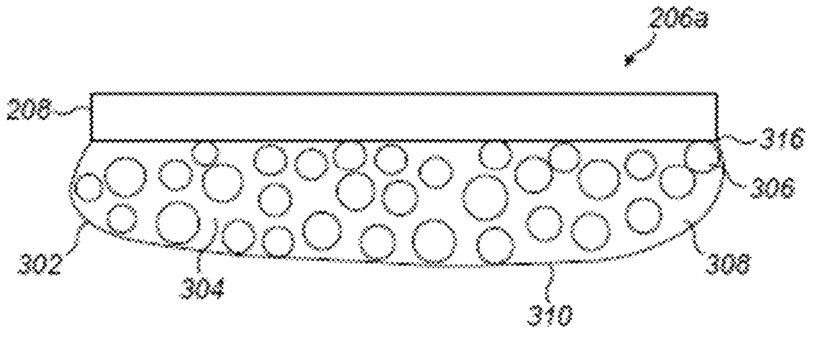
FIG. 6 illustrates a cross section of FIG. 4A along the line A-A where the bladder is of the type illustrated in FIG. 5.

A first example of a bladder 206*a* suitable for the arrangement illustrated in FIG. 4 is illustrated in FIGS. 5 and 6. In both FIGS. 5 and 6 the bladder is in an expanded, or inflated, state. FIG. 5 illustrates the upper surface of the external membrane 302 of the bladder, which is described in more detail below. FIG. 6 illustrates a cross-section of the bladder 206*a* coupled to the planar member 208 as defined by the line A-A in FIG. 4.

The bladder 206*a* comprises an external membrane 302 and an internal cavity 304 defined by the external membrane. The internal cavity 304 comprises a plurality of solid particles 306 and is configured to hold a plurality of fluid particles. In the inflated state illustrated in FIG. 6, the plurality of fluid particles is located in spaces 308 that separate adjacent solid particles 306.

The external membrane 302 comprises a second surface 310 which opposes the bottom surface 316 of the planar member and which is configured to comply with an uneven floor surface that it is in contact with. The bladder 206*a* further comprises an opening 312 in the external membrane 302. The opening is configured to enable the extraction of one or more of the fluid particles from the bladder so as to cause compaction of the bladder. In FIG. 5, the bladder is illustrated as comprising only one opening 312. In alternative examples, it would be understood that the bladder could comprise any number of openings. The opening may be positioned in any location on the external membrane of the bladder.

In FIG. 5, the shape of the bottom of the planar member 208 to which the upper surface of the bladder is coupled is illustrated by dotted lines. These dotted lines serve to demonstrate the comparative shape of upper surface of the external membrane relative to the planar member 208. The shape of the upper surface of the external membrane 302 matches the shape of the bottom surface 316 of the planar member. The term “match” does not necessarily imply that the surface of the external membrane 302 is exactly the same as the shape of the bottom surface 316 of the planar member. Rather, the upper surface of the external membrane 302 may circumscribe the shape of the bottom surface 316 of the planar member. That is, the shape of the upper surface of the external membrane 302 may generally follow the shape of the bottom surface 316 of the planar member. As illustrated in FIG. 5, the upper surface of the external membrane may cover a greater area than the area comprised within the bottom surface 316 of the planar member.

However, the shapes of the upper surface of the external membrane 302 and the bottom surface 316 of the planar member are generally the same. In the example illustrated in FIG. 5, the bottom surface of the planar member 208 has the shape of a quadrilateral. The upper surface of the external membrane 302 has the same quadrilateral shape. More specifically, in FIG. 5, the bottom surface 316 of the planar member is in the shape of a square. The upper surface of the external membrane 302 is also in the shape of a square. In alternative examples the bottom surface of the planar member may be of different shapes. That is, the bottom surface of the planar member may have a triangular, circular or any alternative shape. Irrespective of the specific shape of the bottom surface of the planar member, the upper surface of the external membrane has a shape that is generally the same as the shape of that bottom surface.

The planar member 208 may further comprise one or more apertures through which the moveable elements 210 of the surgical cart can extend. Thus, the moveable elements 210 are not directly connected to the planar member 208 and can be moved independently of both the planar member and the moveable elements 210. The external membrane 302 is shaped so that the bladder 206*a* does not interact with the moveable elements as its level of inflation is varied. More specifically, the upper surface of the external membrane 302 is shaped so that it extends around the one or more apertures, as demonstrated by reference 314. In other words, the apertures are not covered by the external membrane. This arrangement reduces the likelihood of the bladder interfering with the moveable elements when the mechanical brake is not activated.

The number of apertures in the planar member corresponds to the number of moveable elements of the surgical robot. In the example illustrated in FIG. 5, the planar member 208 comprises four apertures. Correspondingly, the external membrane 302 of the bladder is shaped around these four apertures 314 such that a moveable element is able to extend through the bladder without interfering with the bladder. In alternative examples, it would be appreciated that an alternative number of movable elements may be used. Thus, the planar member may comprise an alternative number of apertures, and the bladder may be shaped around this alternative number of apertures 314.

The upper surface of the external membrane 302 illustrated in FIG. 5 covers the entirety of the area of the bottom surface 316 of the planar member. This configuration of bladder is preferable as it maximises the overall surface area of the cart that is covered by the bladder, and therefore the stability that is afforded by the bladder. The bladder can be compacted as described above to an increase the frictional engagement between the plurality of solid particles and conform the bladder to an uneven surface, which thereby stabilises the surgical robot on that surface.

The bladder 206*a* may further comprise a plurality of internal compartments 318 that are separated by one or more internal membranes 316. The internal membranes 316 may be located within the internal cavity of the bladder 206*a*. The internal membranes 316 may act to separate each compartment 318 of the bladder 206*a* from its adjoining compartments 318. The internal membranes 316 may be permeable to the fluid particles but impermeable to the solid particles of the bladders. Thus, fluid particles can move between adjacent compartments 318 through the internal membranes 316 and can therefore be extracted from each of the compartments 318 in the bladder via a single opening 312 in the bladder, irrespective of whether that opening is directly coupled to each compartment 318. However, the solid particles cannot pass through the internal membranes 316 and are therefore confined to their respective compartments 318. Each compartment 318 within the bladder may otherwise be referred to as a pocket.

The incorporation of a plurality of compartments 318 within the bladder 206*a* allows for the distribution of solid particles throughout the bladder to be evenly dispersed. That is, solid particles can be evenly distributed amongst the plurality of compartments 318. The distribution of solid particles prevents the particles from accumulating in one location within the bladder, such as in the middle of the bladder, which would impact the shape of the bladder when it is compacted.

Figure 7:
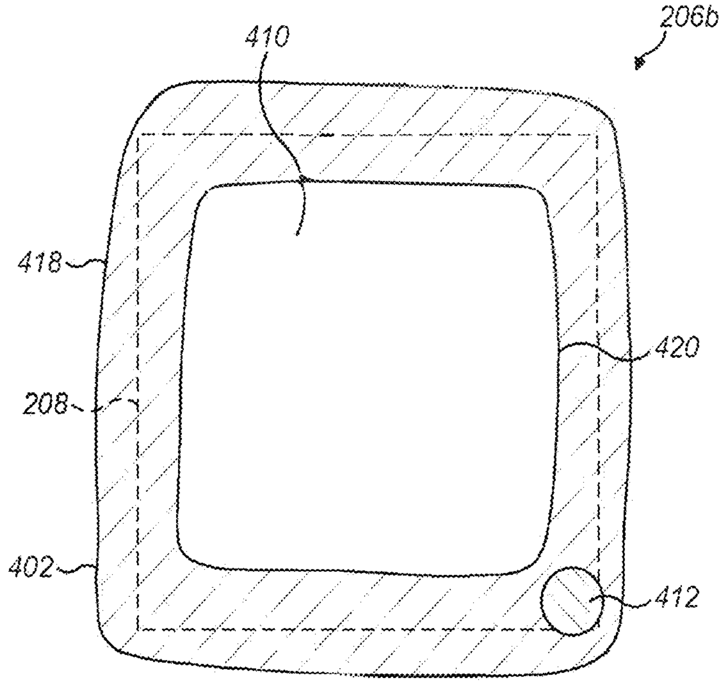
FIG. 7 illustrates a second example of a bladder suitable for the arrangement illustrated in FIGS. 4A and 4B.
Figure 8:
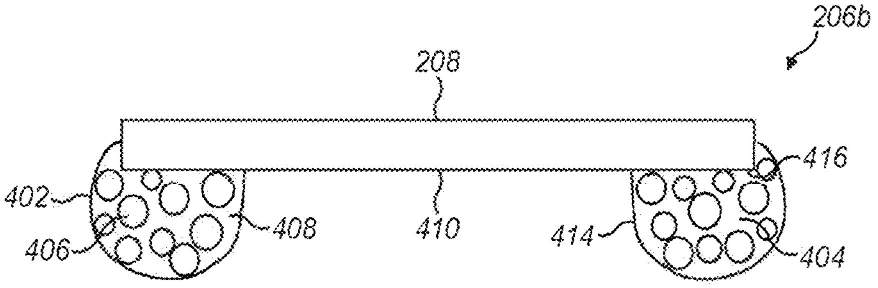
FIG. 8 illustrates a cross section of FIG. 4A where the along the line A-A bladder is of the type illustrated in FIG. 7.

A second example of a bladder 206*b* suitable for the arrangement illustrated in FIG. 4 is illustrated in FIGS. 7 and 8. In both FIGS. 7 and 8 the bladder is in an expanded, or inflated, state. FIG. 7 illustrates the upper surface of the external membrane 402 of the bladder, which is described in more detail below. FIG. 8 illustrates a cross-section of the bladder 206*b* coupled to the planar member 208 as defined by the line A-A in FIG. 4.

As with the first exemplary bladder 206*a*, in FIGS. 7 and 8 the bladder 206*b* comprises an external membrane 402 and an internal cavity 404 defined by the external membrane. The internal cavity 404 comprises a plurality of solid particles 406 and is configured to hold a plurality of fluid particles. In this state, the plurality of fluid particles is located in spaces 408 that separate adjacent solid particles 406.

In FIG. 7, the shape of the bottom of the planar member 208 to which the upper surface of the bladder is coupled is illustrated by dotted lines. These dotted lines serve to demonstrate the comparative shape of the upper surface of the external membrane relative to the planar member 208. The bladder 206*b* is coupled to the bottom surface 416 of the planar member by an upper surface of the external membrane. The upper surface of the external membrane is coupled to the bottom surface 416 of the planar member such that a portion 410 in the middle of the bottom surface of the planar member is exposed. That is, a portion 410 of the bottom surface 416 of the planar member is not covered by the upper surface of the external membrane. The upper surface of the external membrane 206*b* comprises an outer perimeter 418 and an inner perimeter 420. The outer perimeter 418 circumscribes the inner perimeter 420. That is, the outer perimeter 418 is of generally the same shape as the inner perimeter 420 but is larger than the inner perimeter. The upper surface of the external membrane 206*a* therefore forms a ring shape, in which the edges of the bottom surface 416 of the planar member are covered by the membrane but the middle of that bottom portion is not covered by the membrane.

In the example illustrated in FIG. 7, the bottom surface 416 of the planar member has the shape of a quadrilateral. The upper surface of the external membrane 402 has the same quadrilateral shape. More specifically, in FIG. 7, the bottom surface 416 of the planar member is in the shape of a square. The upper surface of the external membrane 402 is also in the shape of a square. In alternative examples the bottom surface of the planar member may be of different shapes. That is, the bottom surface of the planar member may have a triangular, circular or any alternative shape. Irrespective of the specific shape of the bottom surface of the planar member, the upper surface of the external membrane has a shape that is generally the same as the shape of that bottom surface.

The external membrane 402 comprises a surface 414 which opposes the bottom surface 416 of the planar member and which is configured to comply with an uneven surface that it is in contact with. The bladder 206*b* further comprises an opening 412 in the external membrane 402. The opening is configured to enable the extraction of one or more of the fluid particles from the bladder so as to cause compaction of the bladder. The opening may be positioned in any location on the external membrane of the bladder.

The advantage of the bladder 206*b* is that it has a minimised likelihood of interfering with the moveable elements 110, 210 of the surgical cart. That is, the one or more apertures in the planar member through which the one or more moveable elements are configured to retract will be located within the portion 410 of the planar member that is not covered by the bladder. Thus, the disadvantages associated with interactions between the movable elements and the bladder, such as tearing, are reduced.

In FIG. 7, the bladder is illustrated as comprising only one opening 412. In alternative examples, it would be understood that the bladder could comprise any number of openings. For example, the bladder may comprise two openings. The openings may be located on opposing sides of the bladder. The time at which fluid particles are extracted from each opening may differ. For example, a first end of the bladder may be pressurised via a first opening located at the first end, whilst no pressure is applied to a second opening located at the second end of the bladder. The second end of the bladder may also be pressurised via the second opening whilst no pressure is applied to the first opening. If the first opening is pressurised independently of the second opening the pressure differential may be such that, in addition to the extraction of fluid particles via the first opening, solid particles are moved from the second end towards the first end of the bladder. This will mean that, when compacted, the height of the first end of the bladder will be greater than the height of the second end of the bladder, as more solid particles will be accumulated at the first end. This effect can be achieved with any number of openings in the bladder. The height of a bladder is defined as the distance between the upper and lower surfaces of its external membrane. The first exemplary bladder 206*a* may also be adapted to comprise multiple openings to provide a similar effect. The bladder 206*b* may additionally or alternatively comprise one or more internal membranes defining a plurality of compartments as described above with respect to the first exemplary bladder 206*a*.

Figure 9A:
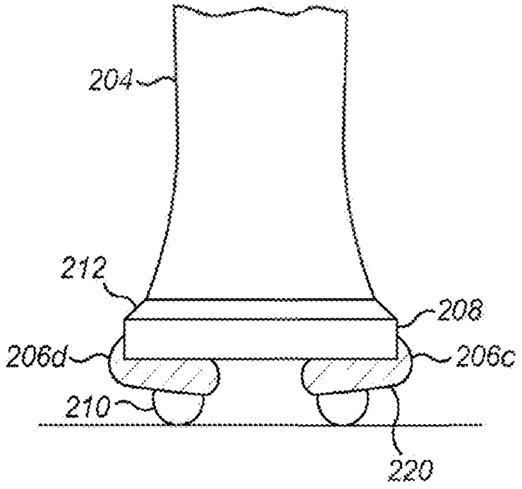
FIGS. 9A and 9B illustrate a third arrangement for supporting a surgical robot on a flat and an uneven surface, respectively.
Figure 9B:
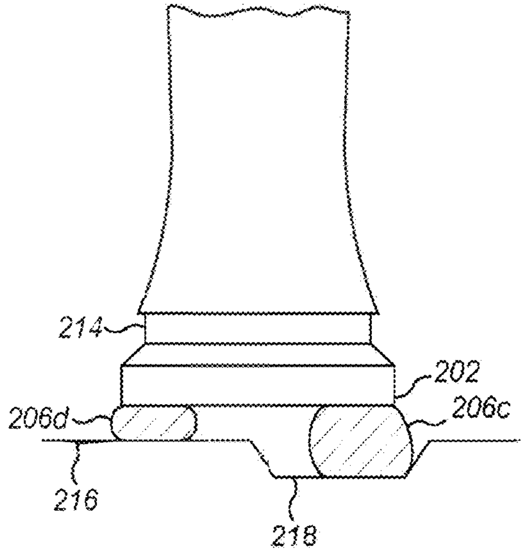
Figure 10:
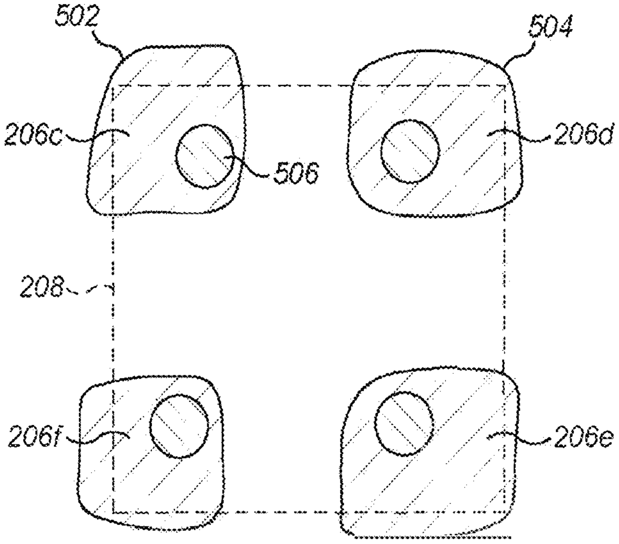
FIG. 10 illustrates a plurality of bladders suitable for the arrangement illustrated in FIGS. 9A and 9B.

A third arrangement for supporting a surgical robot is illustrated in FIGS. 9A, 9B and 10. This arrangement differs from that which is illustrated in FIGS. 4A and 4B in that it comprises a plurality of bladders 206*c-f*. FIG. 9A illustrates a configuration of the lower portion of the surgical cart 204 comprising a plurality of bladders before the mechanical brake system has been actuated or the bladder has been deflated. In this configuration the bladders are in an expanded, or inflated, state. FIG. 9B illustrates the corresponding configuration after the mechanical brake system has been activated, and in which the bladders are in a compacted, or deflated, state. FIG. 10 illustrates the upper surface of the external membrane of the bladders 206*c-f*, which is described in more detail below.

With the exception of its lower portion, the surgical cart 204 illustrated in FIGS. 9A and 9B corresponds to the surgical cart 104 illustrated in FIGS. 1 to 2B. The surgical cart 204 forms part of a surgical robot as illustrated in FIG. 1. The surgical cart 204 comprises a mechanical brake system as described above with respect to FIGS. 2A and 2B. The surgical cart 204 is further coupled to one or more moveable elements 210. The moveable elements 210 are mechanical components that enable the movement of the surgical cart 204 relative to a floor surface. In one example, the one or more moveable elements 210 are wheels.

The bladders 206*c-f* individually correspond broadly to the bladders 206*a* and 206*b*. That is, each bladder 206*c-f* is coupled to the planar member 208 which supports the surgical robot. Each bladder further comprises an external membrane 502, an internal cavity defined by the external membrane and an opening 506 in the external membrane. The internal cavity comprises a plurality of solid particles and is configured to hold a plurality of fluid particles. The external membrane 502 is formed of one or more layers of material and defines a housing within which the remaining features of the internal bladder are located. The external membrane comprises at least two opposing surfaces. Each surface comprises an outer side and an inner side. The inner side of each surface faces the internal cavity. The outer side of each surface faces away from the internal cavity and towards the environment in which the surgical robot is located. The dimensions of the external membrane are such that, when the linear lifting column is in a retracted configuration, each bladder is not in contact with the floor.

The opening 506 of each bladder 206*c-f* is configured to enable the extraction of one or more of the fluid particles so as to cause compaction of that bladder. Each bladder may comprise any number of openings. Each opening may be positioned in any location on the external membrane of the bladder. The pressurisation of each bladder 206*c-f* may be independent of the pressurisation of the remaining bladders.

In FIG. 9B the mechanical brake system is activated, and the bladder deflated whilst the surgical cart is placed on an uneven floor surface. The floor surface comprises a first portion 216 of higher relative elevation and a second portion 218 of lower relative elevation. The planar member 208 and the bladders 206*c-f* are lowered and the moveable elements 210 are retracted, so that the bladders 206*c-f* are placed in contact with the floor surface. More specifically, the second surface 220 of each of the bladders 206*c*-fare in contact with the floor surface. The second surface 220 of each bladder is configured to comply with an uneven surface that it is placed in contact with. In FIG. 9B, the second surface of bladder 206*d* is positioned over the first portion 216 of the surface has adapted to the shape of the first portion. The second surface of bladder 206*c* is positioned over the second portion 218 has adapted to the shape of the second portion. The mechanism of each bladder is as described above with respect to alternative examples of bladders 206*a* and 206*b*, except for that each bladder 206*c-f* may be inflated independently of the other bladders. By varying the pressurisation of each bladder independently, the centre of gravity is located over a central portion of the planar member, and so no tilting of the surgical cart is experienced. Thus, the stability of the cart is ensured.

In FIG. 10, the shape of the bottom of the planar member 208 to which the upper surface of the bladder is coupled is illustrated by dotted lines. These dotted lines serve to demonstrate the comparative shape of the upper surface of the external membrane relative to the planar member 208. FIG. 10 illustrates the upper surface of the external membranes 502 of bladders 206*c-f*, which is described in more detail below.

As described above with respect to FIGS. 5 and 7, the bottom surface of planar member may have a variety of different shapes. However, in preferred examples, the bottom surface of the planar member is formed of a shape that comprises a plurality of vertices. In these preferred examples, each bladder of the plurality of bladders may be coupled to a respective vertex of the bottom surface of the planar member. In FIG. 10, the bottom surface of the planar member 208 has the shape of a quadrilateral, and therefore comprises four vertices 504. The arrangement further comprises four bladders 206*c-f*, where each bladder is coupled to a respective vertex of the planar member 208. It would be appreciated that the bottom surface of the planar member may comprise any alternative number of vertices. The number of bladders may therefore correspond to the number of vertices of the bottom surface of the planar member. That is, a bladder may be coupled to each vertex of the bottom surface of the planar member. It would be appreciated that in alternative examples the bladders may not correspond to the number of vertices of the bottom surface of the planar member. In alternative examples, the bottom surface of the planar member may not have any vertices. In these examples, the number of bladders in the arrangement will be independent on the number of vertices of the bottom surface of the planar member.

An advantage of the arrangement of bladders illustrated in FIGS. 9A to 10 relative to the arrangement illustrated in FIGS. 4A to 8 is that the volume of each individual bladder is reduced. The number of solid particles in each bladder is also reduced. Thus, each bladder can be deflated, or compacted, in less time than larger bladders. In addition to this, in an arrangement where each of the plurality of bladders is coupled to a respective vertex of the bottom surface of the planar member, a suitable clearance can be established between each bladder and the one or more moveable elements of the surgical robot. Thus, as with the bladder 206*a*, the bladders 206*c-f* can be positioned so that the likelihood of them contacting or interfering with the moveable elements is minimised. The probability of the external membrane of a bladder being torn by a moveable element is therefore significantly reduced.

Furthermore, as mentioned above, each bladder 206*c-f* may be pressurised independently of the remaining bladders.

That is, each bladder can be pressurised at a different time to the pressurisation of the remaining bladders. In other words, each bladder can be deflated individually. The independent adjustment of each bladder provides the possibility of raising one side of the surgical cart independently of a second side of the surgical cart, which increases the ease of maneuverability and/or adjustability of the cart.

In the examples of bladders illustrated in FIGS. 6 and 8, the solid particles 306, 406 that are confined within the internal cavity of the bladder form a plurality of independent granular particles, or granules. A granule is defined as a group of solid particles that is formed into a three dimensional shape such as a sphere. The granules are confined within but are free to move around the internal cavity when the fluid particles are also present within the internal cavity. The granules are compacted when the fluid particles are extracted from the internal cavity.

In examples where the solid particles form a plurality of granules, it is important to ensure that friction between the granules and the external membrane of the bladder is low. This ensures that the external membrane is not damaged by compaction or movement of the granules against the inner side of the membrane. However, a lower value of friction between the granules themselves will lead to a decrease in the overall stiffness of the bladder, and therefore less variation in the height of the bladder above the ground between its inflated and deflated states. It is therefore important to select an appropriate material for the solid particles to form the granules so that appropriate coefficients of friction can be met. Examples of appropriate materials that may be used to form the granules are coffee beans, coffee grains, glass beads, glass spheres, metal spheres, sawdust, cubic rubber granules, polycarbonate grains, diatomaceous earth and flexible particles such as styrofoam particles. Of these exemplary materials, those with higher hardness and stiffness properties (such as coffee beans, coffee grains, glass beads, glass spheres and metal spheres) may be preferable due to the weight of the surgical cart that must be supported by the bladder, and by extension the granules. In a specific example, the granules may be formed from coffee beans. Coffee beans have favourably high absolute strength properties, as well as a high strength to weight ratio. The coefficient of static friction for coffee beans may be between 0.3 and 0.6, depending on the exact size of the beans. The average hardness of the beans is 12.34±1.28 gf (0.12N±0.013N), and their average fracturability is 2.45±0.08 gf (0.024N±0.0009 N).

Furthermore, an appropriate size of granule for use in the bladder should be selected. This is because the fluid permeability of the bladder is proportional to the size of the granules within its internal cavity. That is, as the average diameter of the granules in the bladder decreases, the volume of fluid particles that can be located between these granules when the bladder is in an inflated state is greater. Thus, decreasing the average diameter of the granules will increase the time required to extract the one or more fluid particles from the bladder, in order for it to reach a deflated state.

The size of granules should preferably be selected in dependence on the design of the bladder. For bladder designs with larger areas configured to cover the whole of a planar member, such as those illustrated in FIGS. 4A to 8, granules with a larger average diameter are preferable. This is because using granules with smaller diameters would increase the amount of time required to deflate the bladder. In contrast, granules with a smaller average diameter are preferable in designs incorporating more than one bladder, such as that which is illustrated in FIGS. 9A to 10. An exemplary range of average diameter size for the granules to be used in the bladder is between 0.2 mm and 15 mm. Materials such as glass spheres may produce granules with an average diameter at the lower end of this range, at 0.2 mm on average. Materials such as coffee beans may produce granules with an average diameter at the upper end of this range, at 15 mm on average. This is because the volume of each individual bladder is smaller, which means that the time taken for the bladder to reach the deflated state naturally decreases.

When selecting materials for the granules to be used in the bladder, it is also useful to consider the irregularity of the surfaces of the granules provided those materials. Granules with irregular surfaces and high surface friction may be beneficial in some applications, as they will result in a deflated bladder with higher rigidity. Granules with more regular, smoother surfaces may be favourable in other applications as, although they will have a lower strength when compressed together, they will flow within the bladder easier when it is in the inflated state. A balance between the rigidity of granules when the bladder is in the deflated state and their freedom of movement during the inflated state should be considered when selecting optimal materials.

Figure 11:
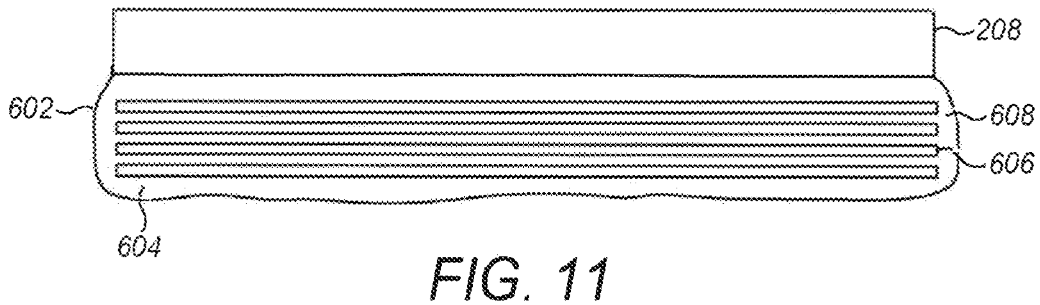
FIG. 11 illustrates a cross section of FIG. 4A along the line A-A for an alternative example of a bladder.

In an alternative example, the solid particles may not form a plurality of granules and may be comprised within a plurality of laminate sheets, or layers of particles. An example of a bladder incorporating this arrangement is illustrated in FIG. 11. FIG. 11 illustrates an alternative arrangement of the internal cavity of the bladder illustrated in FIG. 4. However, this arrangement may be applied to any of the examples illustrated in FIGS. 4A to 10.

The bladder illustrated in FIG. 11 is coupled to the bottom surface of a planar member 208 and comprises an external membrane 602 with an internal cavity 604 being defined by the external membrane. The internal cavity 604 comprises a plurality of laminate sheets 606 and is configured to hold a plurality of fluid particles. In the inflated state illustrated in FIG. 11, the plurality of fluid particles is located in spaces 608 that separate adjacent sheets 606. The laminate sheets 606 may be arranged so that they are substantially parallel to each other within the internal cavity 604. The term "sheet" may be defined as a planar, or substantially flat, element. In FIG. 11, each sheet 606 is formed from a plurality of solid particles. When the fluid particles are removed from the internal bladder, the laminate sheets 606 are compacted against each other and high frictional forces are generated between pairs of adjacent sheets. These high frictional forces strongly couple the sheets together and increase the stiffness of the overall structure of the bladder.

The overall stiffness achieved by the arrangement of laminate sheets illustrated in FIG. 11 is dependent on a number of different factors. These factors include the material from which the solid particles are formed, the number of laminate sheets, the thickness of each sheet and the pressure at which fluid particles are extracted. The material of the external membrane of the bladder may also improve the overall stiffness of a bladder comprising laminate sheets. In one example, the external membrane may be formed of a plastic, such as thermoplastic polyurethane (TPU). This material has been identified as providing promising results when used in combination with a laminate structure of the bladder.

When a bladder as described above with respect to any of the preceding examples is transformed from an inflated state to a deflated state, this transition may result in a change in orientation, or tilting, of the surgical cart. This is because solid particles may be unevenly dispersed within a bladder, and so deflation of the bladder will result in an increased surface area in a first part of the bladder that comprises a large quantity of solid particles when compared to a second part of the bladder that comprises a smaller relative quantity of solid. To mitigate this effect, a mechanism may be provided that may apply a mechanical vibration to the solid particles inside the bladder to encourage their disbursement inside the internal cavity, so that they do not accumulate in a certain portion of the bladder. Thus, the solid particles can be distributed around the bladder as evenly as possible, and the tilting of the surgical cart can be minimised. Adapting the bladder so that it comprises a plurality of internal compartments as described above with respect to FIG. 5 may also mitigate this effect.

It may be advantageous to ensure that the shape of the bladder does not deviate substantially as its pressurisation is varied. That is, the shape, and in particular the outer dimensions, of the bladder should remain substantially constant as its pressurisation is varied. This would ensure that the bladder does not, in one or more portions, extend substantially outside of an area bounded by the bottom surface of the planar member. Thus, the likelihood of the bladder providing a tripping hazard in the operating theatre would be reduced. The likelihood of the external membrane of the bladder being trapped by the moveable elements of the surgical cart as they are retracted would also be reduced.

Figure 12:
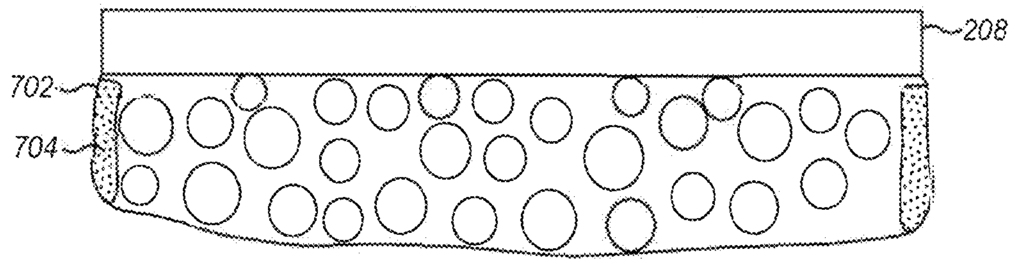
FIG. 12 illustrates a cross section of FIG. 4A along the line A-A for a further alternative example of a bladder.

In order to ensure that the outer dimensions of a bladder do not vary considerably, it may be provided with a secondary, reinforcement material which is attached to its external membrane. An example of a bladder incorporating such reinforcement material is illustrated in FIG. 12. FIG. 12 illustrates an alternative arrangement of the internal cavity of the bladder illustrated in FIG. 6. However, this arrangement may be applied to any of the examples illustrated in FIGS. 4A to 11. The bladder comprises a layer of reinforcement material 704 which is coupled to the inner side of its external membrane 702. The reinforcement material 704 is configured to maintain the shape of the bladder as its level of pressurisation is varied. The reinforcement material may be provided as a single strip that extends around the entirety of the inner side of the external membrane. Additionally, or alternatively, the reinforcement material may comprise one or more strips that are dispersed along the inner surface of the external membrane. Each strip of reinforcement material may be located in an inner pocket located in the inner side of the external membrane. These strips of reinforcement material provide the advantage of enabling a higher degree of frictional engagement between solid particles within the bladder. The reinforcement material can be of any suitable material. An exemplary material to be selected as the reinforcement material is foam. The use of a foam reinforcement material will advantageously even out the shape of the bladder whilst also deforming with the membrane when the bladder is deflated.

The output force of a bladder is defined as the force that it is able to resist. That is, the output force indicates the overall weight that the bladder is able to support, as provided by the surgical robot. The output force of the bladder is proportional to its stiffness. The stiffness of the bladder, in turn, can be varied based on several factors. Such factors include the level of the pressure applied to the bladder, the cross-sectional area of the bladder when inflated, the material properties of the solid particles within the bladder, the number of solid particles located within the bladder (or initial particle density) and the material of the external membrane.

Thus, amongst other factors, it is important to consider the material from which the external membrane of a bladder is to be formed. Whilst the membrane must have a certain level of stiffness in order to support the weight of a surgical cart, it must also be flexible so that it can be deformed as the bladder is varied between an inflated and a deflated state. A balance must be sought between the flexibility of the material and its stiffness. It has been observed that a coefficient of friction of between 0.5 and 1.5 is desirable for optimising flexibility and therefore the deformation of the internal bladder. A more favourable range for the coefficient of friction of the membrane may be between 0.7 and 1.1. In a specific example, the coefficient of friction may be 1. A coefficient of friction of close to 1 is desirable, as this value enables efficient friction and/or suction at small contact angles.

Equally the elasticity of the membrane has been seen to have a positive impact on its deformability. The elasticity of the membrane should be selected in combination with the material properties of the particles to be comprised within the bladder. For example, it may be beneficial to combine particles of a high average hardness with a membrane that has a high degree of flexibility. Similarly, it may be beneficial to combine particles of a lower average hardness with a stiffer membrane. The careful selection of membrane properties with respect to the type of particles comprised within the bladder ensures that the bladder can support the weight of a surgical robot, when necessary, whilst also being able to deform according when the state of the bladder is to be varied.

Examples of materials that can be selected to form the external membrane of any of the bladders disclosed in FIGS. 4A to 12 are plastics such as polythene, latex or silicone and textiles such as polyester and velvet. Where a high value of membrane stiffness is required, polythene may be selected. The young's modulus for polythene is between 600-1500 MPa. By comparison, polyester has a lower young's modulus of approximately 920 MPa, and velvet has a young's modules value of between 18-38 GPa. The use of textiles as an external membrane material has been found to provide favourable bladder characteristics when combined with granules made from coffee beans. These materials are durable, compliant enough to conform to the shape of a floor surface and are able to recover their shape easily. Such characteristics are favourable for the selection of optimal external membrane materials. The external membrane could alternatively be formed from a combination of materials to achieve optimal performance.

The material from which the external membrane is to be formed is also impermeable to solid and liquid particles. The impermeable nature of the external membrane to such particles prevents the absorption of contaminated matter on the floor of the operating theatre by the bladder. Furthermore, it allows the membrane to be cleaned by commonly used cleaning materials without damage being inflicted on the internal structure of the bladder. Thus, the complexity of the methods used to clean the surgical robot is not increased by the addition of a bladder to the robot. The external membrane material may, in one example, allow gases to pass through it when a force is applied to the material. In other words, the membrane may be semipermeable, or impermeable to solid and liquid particles but permeable to gas particles. The advantage of a semipermeable membrane is that it allows the bladder to be inflated and deflated through natural gas movement in and out of the bladder, without the application of a vacuum to the bladder. In an alternative example, the external membrane material may be completely impermeable, or nonporous. That is, the material may be impermeable to all particles, including gas particles. An advantage of a nonporous membrane material is that it allows for high pressure values to be reached inside the bladder when a vacuum is used to inflate and deflate the bladder.

The bladders illustrated in FIGS. 4A to 12 may be permanently coupled to the bottom surface of the planar member 208. That is, the bladders may be non-removable with respect to the planar member, and therefore the surgical robot, once they have been assembled onto the planar member. Alternatively, the bladders may be removably coupled to the bottom surface of the planar member. That is, the bladders may be detached from the planar member and therefore the surgical robot. An advantage associated with the removeable nature of the bladders is that they can be replaced, if necessary, due to damage or wear of the bladder. A further advantage is that removing the bladders means that the bottom of the surgical robot can be more easily accessed for cleaning.

The fluid particles that are held within and extracted from the bladder may be liquid particles or gas particles. In a preferred example, the fluid particles are gas particles. Gas particles can be extracted from and inserted into the bladder with greater ease than fluid particles. In a further example, the fluid particles may be air particles. Air particles are preferable fluid particles to be extracted from the bladder as they are readily available. That is, air can be obtained from the environment in which the surgical robot is located to be pumped into the bladder and can be exhausted into the atmosphere in order to deflate the bladder.

Figure 13:
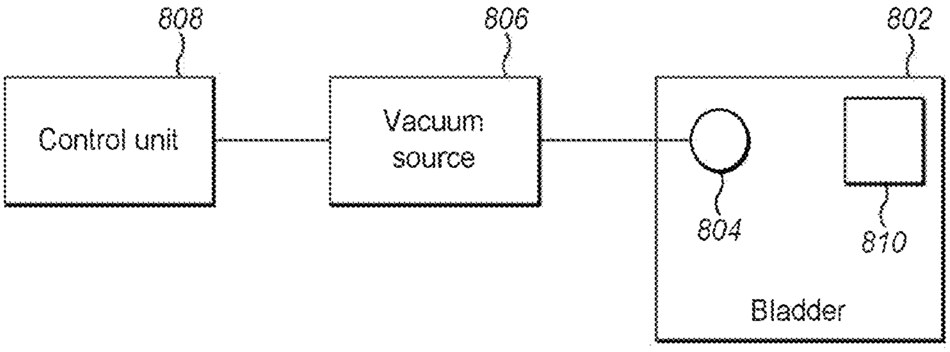
FIG. 13 illustrates a system for controlling the pressurisation of the bladders illustrated in FIGS. 4A to 12.

A system for controlling the level of pressurisation of a bladder as illustrated in FIGS. 4A to 12 is illustrated in FIG. 13. The system comprises a bladder 802 with an opening 804, a vacuum source 806 and a control unit 808. The bladder 802 may be of any suitable design as described above with reference to FIGS. 4A to 12.

The vacuum source 806 is mechanically coupled to the bladder 802 via the opening 804. In other words, the vacuum source 806 is coupled to the opening 804 of the bladder 802. The vacuum source 806 is configured at least to extract one or more of the fluid particles from the bladder. The vacuum source 806 may additionally be configured to insert one or more fluid particles into the bladder 802.

In one example, the vacuum source 806 is an electrically actuated vacuum pump. The vacuum pump may be actuated using a switch located at the surgeon's console in the surgical robotic system. The vacuum pump is configured to apply a negative pressure inside the bladder. That is, the vacuum pump is configured to apply a negative pressure within the internal cavity that is defined by the external membrane of the bladder. The vacuum pump may be a one-way vacuum pump. That is, the vacuum pump may be configured to provide only a negative pressure to the bladder. In other words, the vacuum pump may be configured only to deflate the bladder. An advantage associated with the use of a one-way pump is that it minimises the power consumption of the bladder assembly, and therefore overall power consumption of an operating theatre in which the surgical robot is located.

The electrically actuated vacuum pump may alternatively be a two-way pump, or a reversible air vacuum pump. That is, the vacuum pump may be configured to provide both a negative and a positive pressure to the bladder. In other words, the vacuum pump may be configured to both inflate and deflate the bladder. An advantage associated with the use of a two-way pump is that it would enable the stiffness of the bladder to be dynamically adjusted with ease. That is, the bladder could be reinflated by actively pumping air into the bladder, which would be faster than allowing it to reinflate by exposing the inside of the bladder to external air pressure. Thus, a two-way pump provides the possibility of easily re-positioning the surgical cart. Where the vacuum pump is a two-way pump, and the arrangement of bladders comprises a plurality of bladders as illustrated in FIG. 10, the system may be configured to apply a different pressure to each of the bladders in order to achieve a different level of inflation for each bladder.

In a further example, the vacuum source 806 is a mechanically actuated pump. An advantage with a mechanically actuated pump is that it can be easily actuated by any person in the operating theatre. A further advantage is that it is easy to validate a mechanically applied command to inflate the bladder. That is, it is easy to determine that a lever has been moved from a first position A to a second position B, and therefore that actuation of the pump has been commanded. However, the amount of force that can be provided by a mechanical pump is relatively low when compared to an electrically actuated pump. Thus, the level of deflation that can be provided by a pump is limited. To account for this limitation, a spring-loaded lever can be used which reduces the force required to actuate the pump.

The system further comprises a control unit 808 that is coupled to the vacuum source 806. In one example the control unit 808 is electrically coupled to the vacuum source 806. In another example the control unit 808 is mechanically coupled to the vacuum source 806. In the example illustrated in FIG. 13 the control unit 808 is coupled to the bladder 802 via the vacuum source 806. In an alternative arrangement the control unit 808 may be positioned between the vacuum source 806 and the bladder 802, such that the vacuum source 806 is coupled to the bladder via the control unit 808. The control unit 808 is configured to control the extraction of one or more of the fluid particles from the bladder 802.

In one example, the control unit is an electrical control unit. For example, the control unit may be implemented in software and actuated via an electrical command generated by the operator at the surgeon's console. Alternatively, the control unit may be configured in electrical hardware within either the surgeon's console or the surgical robot. In an alternative example, the control unit is a mechanical control unit. That is, the control unit is manually operated by a user. For example, the control unit may be a pedal or a lever. The lever may be implemented as a foot pedal that is coupled to the bottom of the surgical cart. An advantage of the control unit being a mechanical control unit is that it can be operated when no electrical power is being provided to the surgical robot. In addition to this, as mentioned above, a manual control unit can be accessed by a person in the operating theatre, and not just the operator at the surgeon's console.

It would be appreciated that the system illustrated in FIG. 13 may comprise more than one bladder, as described above with reference to FIGS. 9A to 10. In one example, where the system comprises more than one bladder, each bladder comprises its own opening 804, and the vacuum source 806 is coupled to each bladder via its respective opening. In an alternative example, each bladder may comprise its own vacuum source. The control unit 808 may control the vacuum power to be applied to each bladder independently.

The vacuum source 806 may be manufactured together with the bladder 802, such that the vacuum source and the bladder are provided together as a single unit. Alternatively, the control unit 808 may be manufactured together with the bladder 802, and the vacuum source 806 may be provided as a separate component. In a further example, the bladder 802 is manufactured and provided independently of both the control unit 808 and the vacuum source 806.

The bladders 802 may further comprise one or more sensors 810. The sensors may be force sensors or pressure sensors. The sensors are configured to detect when the one or more bladders are in contact with the floor surface. The sensors 810 are therefore preferably located on the second surface of the external membrane, such that they come into contact with the floor surface when the bladder is lowered towards the surface. In one example, each bladder comprises one sensor. In an alternative example, each bladder comprises a plurality of sensors. The sensors 810 may be electrically connected to the control unit 808 such that they form a closed loop control system with the control unit and the vacuum source 806. Thus, the control unit 808 is configured to receive electrical signals from the one or more sensors 810, which indicate the force or pressure values measured by the sensors. An advantage associated with the use of one or more sensors is that it ensures that each bladder is contacting the floor before the vacuum source is activated. In other words, the sensors can be used to ensure that it is appropriate for the bladder to be deflated.

Where the control unit 808 is an electrical control unit, the system described in FIG. 13 may be configured to automatically initiate the process of extracting fluid particles from the one or more bladders when a predetermined value is exceeded. The predetermined value may be a predetermined force value. This force value is measured by the one or more sensors 810 coupled to the bladders. The predefined force value may be established using the known weight of the surgical robot to be supported by the bladder. The predefined force value will be divided between the number of bladders that are coupled to the surgical robot, as each bladder should be configured to support a fraction of the weight of the robot. When a force measurement detected by one of the one or more sensors 810 reaches the predefined force value, this control unit may receive an electrical signal from the sensor indicating that measurement and determine that that bladder is in contact with the floor surface. Thus, the control unit 808 may subsequently send a signal to the vacuum source 806 to actuate the vacuum source and initiate deflation of the bladder 802. It is possible that, where multiple bladders are coupled to the planar member of the surgical robot, the weight of the surgical robot is unevenly distributed amongst those bladders. In this instance, the predefined force value can be set to a very low value so that any contact of a bladder with the floor surface will result in the control unit being configured to activate the vacuum source. It would be appreciated that, in an alternative example, the predetermined value may be a predetermined pressure value.

Figure 14:
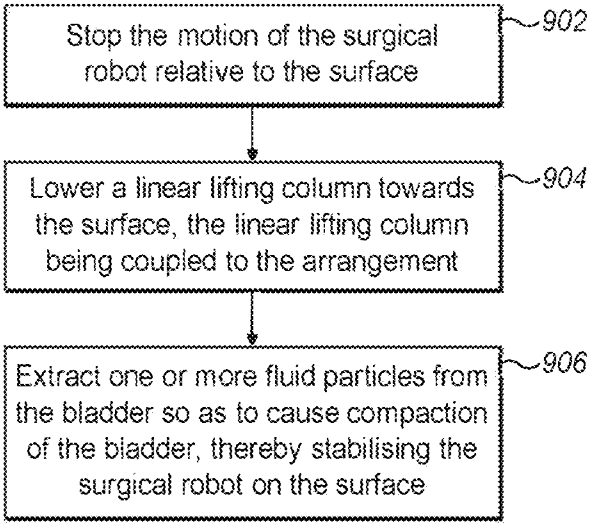
FIG. 14 illustrates a method for stabilising a surgical robot on an uneven surface.

FIG. 14 illustrates a method for stabilising a surgical robot on an uneven floor surface. The surgical robot incorporates an arrangement as illustrated in any of FIGS. 4A to 12. The method is initiated when the surgical robot has been moved to a desired position. The desired position may, for example, be appropriate for commencement of a surgical procedure. The method of stabilising the surgical robot as illustrated in FIG. 14 is completed, in operation, before the initiation of the surgical procedure. The method may alternatively be performed during training or testing of a surgical robotic system. In either case, the method does not itself form part of a surgical procedure.

Once the robot has been moved to its desired position, at step 902 the motion of the surgical robot relative to the floor surface on which it is moving is stopped. The stopping of the surgical robot is instigated by a mechanical brake system. The mechanical brake system is described above with reference to FIGS. 2A and 2B. In one example, the mechanical brake system is activated by an operator. In this example the brake system may be connected to an interface such as a button or a lever than enables the system to be actuated by the operator. In another example, the brake system may be automatically activated. That is, the robot may be configured to detect when it has reached its desired position and may apply the brake system independently of any input from an operator.

Once the motion of the robot relative to the floor surface has been stopped, then at step 904 the linear lifting column of the mechanical brake system is lowered towards the floor surface. The linear lifting column is coupled to the arrangement as described with reference to FIGS. 4A to 12. That is, the arrangement comprises a planar member which supports the surgical robot, and a bladder coupled to a bottom surface of the planar member. The bladder comprises an external membrane having a surface which opposes the bottom surface of the planar member, and which is configured to comply with an uneven surface that it is in contact with an internal cavity defined by the external membrane and holding a plurality of solid particles. The internal cavity is further configured to hold a plurality of fluid particles. The bladder further comprises an opening in the external membrane that is configured to enable the extraction of one or more of the fluid particles so as to cause compaction of the bladder.

When the bladder contacts the surface, it deforms according to the shape of the floor surface, so as to conform to this shape. In other words, the bladder contacts and conforms to the floor surface, thereby stabilising the surgical robot on the surface.

The method illustrated in FIG. 14 further comprises an optional step 906 wherein, with the bladder conformed to the shape of the surface with which it is in contact, one or more fluid particles are extracted from the bladder so as to cause compaction of the bladder. The compaction of the bladder causes an increased frictional engagement between the plurality of solid particles that are located within the bladder, which thereby further stabilises the surgical robot on the surface. The vacuum source may be a form of electrical vacuum pump, or a mechanical pump, as described above. The vacuum pump acts to extract the fluid particles from the bladder, resulting in the compaction of the bladder which further stabilises the surgical robot on the surface. Step 906 may be manually or electrically initiated. For example, step 906 may be initiated by a user depressing a lever or a pedal, by an electrical command being sent from a surgeon's console, by a closed loop command signal generated from sensor measurements or by any other suitable mechanism.

As described above, the surgical robot illustrated in FIGS. 4A and 4B further comprises one or more moveable elements 210. The moveable elements enable the movement of the surgical cart relative to a floor surface. The moveable elements are also capable of being retracted independently of the planar member and the bladder. The method illustrated in FIG. 14 may further comprise retracting the one or more moveable elements of the surgical robot. In one example, the moveable elements are retracted after the compaction of the bladder. That is, the mechanism for actuating the compaction of the bladder is independent of the mechanical brake system of the surgical cart. This timing is advantageous as it allows for the bladder to contact the floor surface whilst the moveable elements are still in contact with the surface. Thus, the bladder is fully in contact with the floor before compaction begins. This means that stability of the cart whilst the support for the weight of the surgical robot is alternated between the moveable elements and the bladders is ensured.

In an alternative example, the one or more moveable elements may be retracted at the same time as the compaction of the bladder. That is, the bladder is compacted during the transition of weight of the surgical cart between the brake and the bladder. This is advantageous because it reduces the overall time required for the surgical robot to be stabilised after the mechanical brake system is activated.

Whilst the examples of the invention illustrated in FIGS. 1 to 12 indicate that the surgical robot comprises a cart with moveable elements, it would be appreciated by the skilled person that the arrangements illustrated herein can equally be coupled to a surgical cart that does not comprise any moveable elements. In this configuration, whilst the surgical robot cannot be easily moved, its stability can still be optimised by incorporating a bladder that can conform to the floor surface with which it is in contact.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description, it will be evident to a person skilled in the art that various modifications may be made within the scope of the invention.

The invention claimed is:

1. An arrangement configured to support a surgical robot, the arrangement comprising:

a planar member on which the surgical robot is supported;

a bladder coupled to a bottom surface of the planar member, the bladder comprising:

an external membrane having a surface which opposes the bottom surface of the planar member, and which is configured to comply with an uneven surface that it is in contact with;

an internal cavity defined by the external membrane, the internal cavity holding a plurality of solid particles and being configured to hold a plurality of fluid particles; and an opening in the external membrane, the opening being configured to enable the extraction of one or more of the fluid particles so as to cause an increased frictional engagement between the plurality of solid particles, thereby stabilizing the surgical robot on the uneven surface;

wherein the planar member includes one or more apertures such that a moveable element is able to extend through each aperture, and the external membrane is shaped so that the bladder does not interfere with the moveable elements as its level of pressurization is varied.

2. The arrangement as claimed in claim 1, wherein the bladder is coupled to the bottom surface of the planar member by an upper surface of the external membrane, and wherein the shape of the upper surface of the external membrane matches the shape of the bottom surface of the planar member.

3. The arrangement as claimed in claim 1, wherein the bladder is coupled to the bottom surface of the planar member by an upper surface of the external membrane such that a portion in the middle of the bottom surface of the planar member is exposed.

4. The arrangement as claimed in claim 1, wherein the one or more apertures comprises four apertures.

5. The arrangement as claimed in claim 1, wherein the internal cavity further comprises a plurality of compartments and one or more internal membranes separating each compartment from its adjoining compartments, the one or more internal membranes being permeable to the fluid particles but impermeable to the solid particles.

6. The arrangement as claimed in claim 1, the arrangement being further configured to apply a first pressure to a first end of the bladder that is different to a second pressure that is applied to a second end of the bladder.

7. The arrangement as claimed in claim 1, wherein the arrangement comprises a plurality of bladders, and wherein the level of pressurization of each bladder is independent of the level of pressurization of the remaining bladders.

8. The arrangement as claimed in claim 7, wherein the bottom surface of the planar member comprises a plurality of vertices and each bladder of the plurality of bladders is coupled to a respective vertex.

9. The arrangement as claimed in claim 1, wherein the one or more bladders are removably coupled to the bottom surface of the planar member.

10. The arrangement as claimed in claim 1, wherein the one or more bladders further comprise a reinforcement material attached to the external membrane, the reinforcement material being configured to maintain the shape of the bladder as its level of pressurization is varied.

11. The arrangement as claimed in claim 1, wherein the plurality of solid particles are independent granular particles.

12. The arrangement as claimed in claim 1, wherein the plurality of solid particles form a plurality of layers of particles.

13. The arrangement as claimed in claim 1, further comprising one or more sensors configured to detect when the one or more bladders are in contact with the surface.

14. The arrangement as claimed in claim 1, wherein the planar member is coupled to a mechanical brake system that comprises a linear lifting column that is coupled to an upper surface of the planar member.

15. The arrangement as claimed in claim 14, wherein the dimensions of the external membrane are such that, when the linear lifting column is in a retracted configuration, the one or more bladders are not in contact with the surface.

16. The arrangement as claimed in claim 1, further comprising a vacuum source coupled to the opening and configured to extract one or more of the fluid particles from the bladder.

17. A method for stabilizing a surgical robot on an uneven surface, the method comprising:

stopping the motion of the surgical robot relative to the surface; and lowering a linear lifting column towards the surface, the linear lifting column being coupled to an arrangement comprising a planar member on which the surgical robot is supported, wherein the planar member includes one or more apertures such that a movable element is able to extend through each aperture, and a bladder coupled to a bottom surface of the planar member, the bladder including: an external membrane having a surface which opposes the bottom surface of the planar member and which is configured to comply with an uneven surface that it is in contact with, an internal cavity defined by the external membrane and holding a plurality of solid particles and being configured to hold a plurality of fluid particles and an opening in the external membrane that is configured to enable the extraction of one or more of the fluid particles such that the bladder contacts and conforms to the surface, thereby stabilizing the surgical robot on the surface, and wherein the external membrane is shaped so that the bladder does not interfere with the movable elements as its level of pressurization is varied.

18. The method as claimed in claim 17 further comprising, when the bladder contacts and conforms to the surface, extracting one or more fluid particles from the bladder so as to cause an increased frictional engagement between the plurality of solid particles.

* * * * *